US011067509B2

(12) United States Patent
Osman

(10) Patent No.: US 11,067,509 B2
(45) Date of Patent: Jul. 20, 2021

(54) FLUORESCENT MICROSCOPE

(71) Applicant: Indiana University Research and Technology Corporation, Indianapolis, IN (US)

(72) Inventor: Hany Osman, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 599 days.

(21) Appl. No.: 15/739,154

(22) PCT Filed: Jun. 30, 2016

(86) PCT No.: PCT/US2016/040527
§ 371 (c)(1),
(2) Date: Dec. 21, 2017

(87) PCT Pub. No.: WO2017/007690
PCT Pub. Date: Jan. 12, 2017

(65) Prior Publication Data
US 2020/0041415 A1    Feb. 6, 2020

Related U.S. Application Data

(60) Provisional application No. 62/188,912, filed on Jul. 6, 2015.

(51) Int. Cl.
*G01N 21/64* (2006.01)
*G02B 7/00* (2021.01)
(Continued)

(52) U.S. Cl.
CPC ......... *G01N 21/6458* (2013.01); *A61B 90/20* (2016.02); *G02B 7/004* (2013.01); *G02B 21/16* (2013.01); *A61B 18/20* (2013.01); *A61B 18/203* (2013.01); *A61B 2017/00486* (2013.01); *A61B 2018/00577* (2013.01); *A61B 2018/00982* (2013.01); *G02B 21/26* (2013.01)

(58) Field of Classification Search
CPC .... G01N 21/6458; A61B 90/20; A61B 18/20; A61B 18/203; A61B 2017/00486; A61B 2018/00577; A61B 2018/00982; G02B 7/004; G02B 21/16; G02B 21/26
See application file for complete search history.

(56) References Cited

U.S. PATENT DOCUMENTS 4,666,239 A    5/1987  Lidholt
4,802,726 A    2/1989  Palmquist et al.
(Continued)

OTHER PUBLICATIONS

Pierce, Mark, et al., "High-resolution Fiber-optic Microendoscopy for in situ Cellular Imaging", Journal of Visualized Experiments (JOVE); www.jove.com, e2306, Jan. 1, 2011, Issue 47; 5 pages.
(Continued)

*Primary Examiner* — Collin X Beatty
(74) *Attorney, Agent, or Firm* — Faegre Drinker Biddle & Reath LLP

(57) ABSTRACT

The present disclosure provides a method and system including a non-confocal microscope with an attached imaging fiber optic for direct and real time in-situ visualization of mammalian microscopic structures for diagnostic and therapeutic uses.

20 Claims, 11 Drawing Sheets

(51) Int. Cl.
*G02B 21/16* (2006.01)
*A61B 90/20* (2016.01)
*A61B 18/20* (2006.01)
*G02B 21/26* (2006.01)
*A61B 18/00* (2006.01)
*A61B 17/00* (2006.01)

(56) References Cited

U.S. PATENT DOCUMENTS

| | | | |
|---|---|---|---|
| 5,459,564 A | 10/1995 | Chivers | |
| 9,335,532 B2* | 5/2016 | Kenny | G02B 21/32 |
| 9,841,579 B2* | 12/2017 | Baribault | H04N 5/2254 |
| 2001/0049258 A1 | 12/2001 | Erdogan et al. | |
| 2002/0045811 A1* | 4/2002 | Kittrell | A61B 1/00096 |
| | | | 600/407 |
| 2004/0001253 A1 | 1/2004 | Abe et al. | |
| 2005/0024721 A1 | 2/2005 | Storz et al. | |
| 2005/0168810 A1 | 8/2005 | Vodyanoy et al. | |
| 2005/0237605 A1* | 10/2005 | Vodyanoy | G02B 21/16 |
| | | | 359/385 |
| 2005/0258376 A1 | 11/2005 | Takatsuka et al. | |
| 2006/0257993 A1* | 11/2006 | McDevitt | G01N 21/6428 |
| | | | 435/287.2 |
| 2007/0291798 A1* | 12/2007 | Kenny | G02B 21/06 |
| | | | 372/6 |
| 2008/0019656 A1* | 1/2008 | Zhou | G02B 6/3833 |
| | | | 385/136 |
| 2010/0290744 A1* | 11/2010 | Zhou | G02B 6/3833 |
| | | | 385/89 |
| 2012/0062987 A1* | 3/2012 | Hnatkovich | G02B 21/24 |
| | | | 359/385 |
| 2013/0038864 A1 | 2/2013 | Flora et al. | |
| 2014/0036258 A1 | 2/2014 | Nakamura et al. | |
| 2014/0063598 A1 | 3/2014 | Zhou et al. | |
| 2014/0082775 A1 | 3/2014 | Zahl | |
| 2014/0187967 A1* | 7/2014 | Wood | A61B 5/0077 |
| | | | 600/473 |
| 2014/0192405 A1* | 7/2014 | Jaffe | G02B 27/30 |
| | | | 359/379 |
| 2014/0268109 A1* | 9/2014 | Eckman | G01M 11/30 |
| | | | 356/73 |
| 2014/0268318 A1 | 9/2014 | Mandella et al. | |
| 2015/0338583 A1 | 11/2015 | Valencia | |
| 2016/0341904 A1 | 11/2016 | Morin-Drouin et al. | |
| 2017/0035275 A1 | 2/2017 | Yajima et al. | |

OTHER PUBLICATIONS

International Search Report and Written Opinion issued by the ISA/US, Commissioner for Patents, dated Nov. 15, 2016, for International Application No. PCT/US2016/040527; 6 pages.

International Search Report and Written Opinion issued by the ISA/US, Commissioner for Patents, dated Sep. 23, 2016, for International Application No. PCT/US2016/ 041131; 7 pages.

International Preliminary Report on Patentability received for PCT Patent Application No. PCT/US2016/040527, dated Jan. 18, 2018, 7 pages.

International Preliminary Report on Patentability received for PCT Patent Application No. PCT/US2016/041131, dated Jan. 18, 2018, 9 pages.

\* cited by examiner

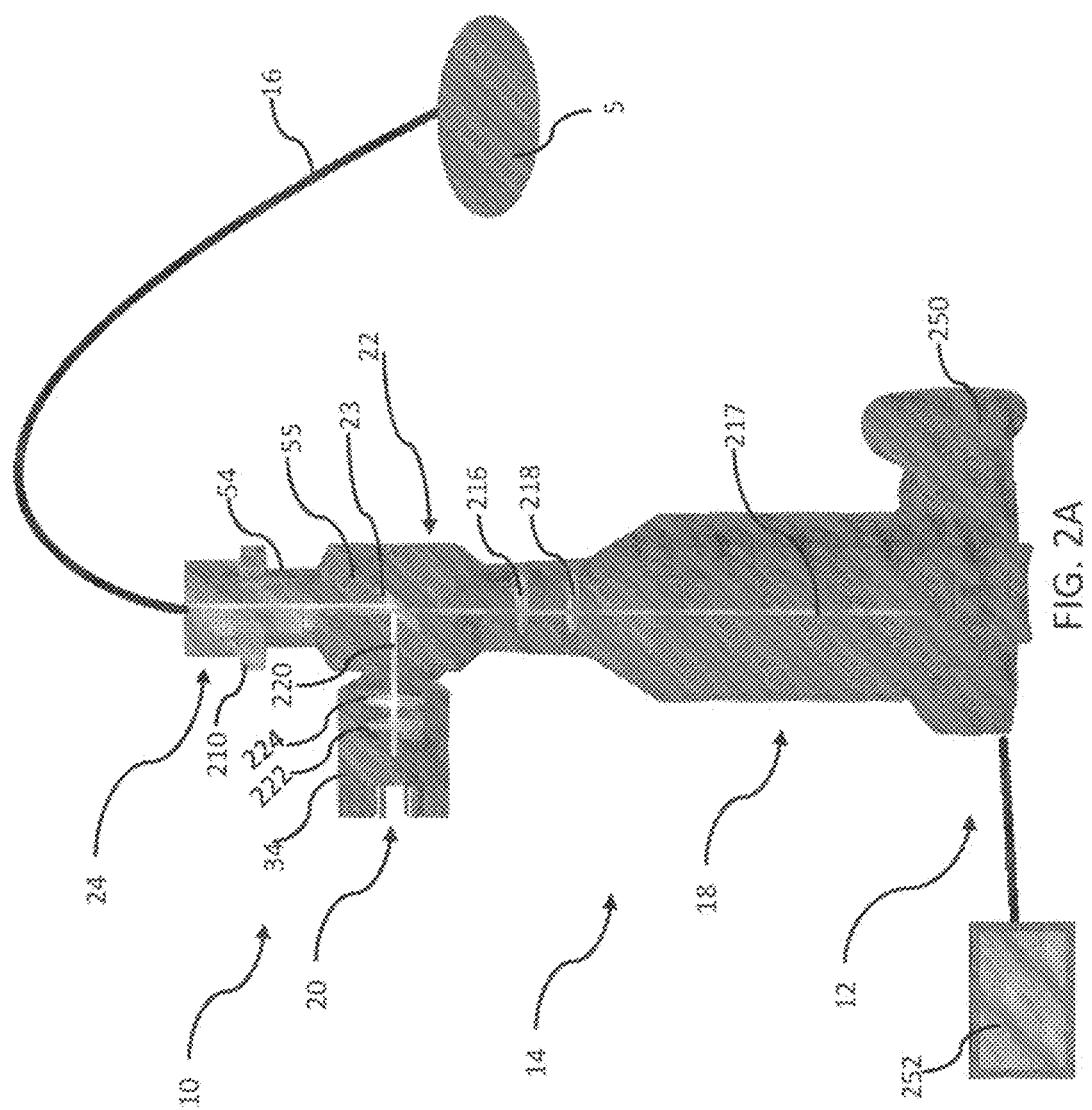

FLUORESCENT MICROSCOPE

CROSS-REFERENCE TO RELATED APPLICATIONS

This application is a U.S. National Stage Application of International Patent Application No. PCT/2016/040527, filed Jun. 30, 2016, which claims the benefit of U.S. Provisional Patent Application Ser. No. 62/188,912, filed Jul. 6, 2015, each of which is expressly incorporated by reference in its entirety.

FIELD OF THE DISCLOSURE

This present disclosure generally relates to fluorescent microscopes and more specifically to a non-confocal microscope with an attached imaging fiber optic for direct and real time in-situ visualization of microscopic structures for diagnostic uses as well as direct and simultaneous tissue treatment for therapeutic uses, and methods of using the same. The methods may be undertaken in-vivo or ex-vivo. The methods may be non-invasive.

BACKGROUND OF THE DISCLOSURE

Obtaining biopsy samples or removal of pathologies and tumors from patients normally relies primarily on the gross evaluation, (either visual, palpation, or other gross methods) of the area to be biopsied or removed. Microscopic confirmation or validation of the biopsy or removed tissue occurs after the pathologist obtains the specimen. The processing of pathology samples is conventionally done through a multi-step process that includes grossing, tissue fixation, processing, embedding, cutting and staining before the tissue is viewable under the microscope. This process often requires several hours. Also, a similar process known as "frozen sections" involves the same steps, however may be performed in several minutes.

Current sampling and excisional methods of both live or ex-vivo tissues lack the ability to screen, visualize or confirm the sample microscopically during or before submitting a sample. Methods include, but are not limited to, obtaining biopsies, ablative treatments removing tumors with no residual tumor at margins, and sampling tissue by gross pathological evaluation. Furthermore, there currently does not exist a method for simultaneous fiber optic in-vivo or ex-vivo pathologic examination for diagnosis and treatment using an ablative energy source such as laser. The ability of simultaneously diagnosing and treating tissue in the same session without the need to displace or replace the apparatus may enhance treatment precision and completeness. Failure of accurate diagnosis or treatment may result in inaccuracies during sampling and inaccurate pathological evaluation of specimens that may result in patient harm. Accordingly, a simple method for visualizing and treating specimens in-vivo or ex-vivo without any significant alteration of the specimen and in real-time for guiding biopsy, tissue removal or sampling is needed. Such a method (and corresponding apparatus) may reduce sampling or excisional errors or eliminate the need for a biopsy or physical sampling of a specimen.

SUMMARY OF THE DISCLOSURE

In one aspect, the present disclosure provides a method for evaluating an in-vivo or ex-vivo specimens, comprising applying a fluorescent dye to the specimen, routing light having a wavelength that causes the dye to fluoresce through a magnifying objective, and through an imaging fiber optic coupled to the magnifying objective and having a tip disposed adjacent the specimen, routing light emitted from the specimen through the imaging fiber optic and the magnifying objective to an image acquisition device coupled to the magnifying objective; and generating an image of the specimen using the image acquisition device. The methods may be undertaken in-vivo or ex-vivo. The methods may be non-invasive.

The methods are not particularly limited in regards to fluorescent or source of dye. For example, in various aspects, the fluorescent dye comprises an acridine orange fluorescent dye. Similarly, in some aspects, the light may be produced from a variety of sources, such as a light emitting diode. Furthermore, in various aspects, the light from the light emitting diode may also be filtered.

In various aspects, the fiber optic may include a bundle of multiple smaller optic fibers, which may allow for the image transmitted to be in its native three dimensional state. The fiber optic may include an optical apparatus such as lens or mirror at its distal tip for further magnification or reflection of light.

Additional exemplary methods disclosed herein may include methods for evaluating a specimen, including routing light having a wavelength that causes a fluorescent dye applied to a specimen to fluoresce through a microscope having an imaging fiber optic coupled to a magnifying objective and having a distal tip disposed adjacent the specimen, routing light emitted from the specimen through the microscope to the magnifying objective, and generating an image of the specimen using an image acquisition device. The methods may be undertaken in-vivo or ex-vivo. The methods may be non-invasive.

Also disclosed are various microscopes. According to various aspects, microscopes may include a light source housing comprising a light emitting diode, a dichroic filter housing, an objective in optical communication with a fiber optic forming an image acquisition axis, filter and lens trays and a tube configured to mechanically communicate with an image acquisition device. Furthermore, in some aspects, the microscope may also include a heat sink in mechanical communication with the light source housing.

In various aspects, the filter housing may include a dichroic mirror and holder, which—in some aspects—may form an angle of about 45 degrees with the image acquisition axis. The angle of the dichroic mirror may be adjustable by rotating the dichroic mirror holder.

In some aspects, the microscope may be configured to form an angle of about 90 degrees between the image acquisition axis and an excitation light produced from the light emitting diode.

Also, placement of the objective may be placed in line with the image acquisition axis.

In some exemplary aspects, the fiber optic may be attached to a fiber optic holder configured to move along the image acquisition axis. The fiber optic holder may be configured to move along the image acquisition axis via a screw mechanism allowing for vertical focusing movement in some aspects. Also, the fiber optic may be moved in axes perpendicular to the image acquisition axis via positioning screws to allow for fine positioning of the fiber optic base within the objective field of view.

The fiber optic is not particularly limited and may comprise a single optic fiber or, in some aspects, may comprise a bundle of multiple optic fibers.

In various aspects, the microscopes may include a variety of filters and/or lenses. In some aspects, the microscope may include a filter between the light source and the image acquisition axis. In some aspects, a condensing lens may be between the light source and the image acquisition axis. Also in other aspects additional light source channels may be added to the system to allow for multiple excitation/emission wavelengths per image, or allow the addition of simultaneous ablative energy sources such as an ablative laser. Light and or energy emitted from these additional channels are routed in a similar fashion through a mirror or dichroic mirror into the image acquisition axis. Light from the additional channels is then carried through the same optic route that includes the magnifying apparatus and fiber optic.

Also, in various aspects, the tube may be configured to accommodate a placement of at least one of a magnifying tube lens, an emission filter, or both. Moreover, the tube may be configured, via tray in one aspect, to interchange magnifying tube lenses, emission filters, or both.

There is also provided a method for evaluating a specimen, comprising routing light having a wavelength that causes a fluorescent dye applied to a specimen to fluoresce through a microscope having an imaging fiber optic coupled to a magnifying objective and having a distal tip disposed adjacent the specimen, routing light reflected from the specimen through the microscope to the magnifying objective, and generating an image of the specimen using an image acquisition device, wherein the microscope comprises a light source housing comprising a light emitting diode, a filter cube, the magnifying objective in optical communication with the imaging fiber optic forming an image acquisition axis, and a tube configured to mechanically communicate with the image acquisition device.

In any of the aspects or aspects of the present invention, the specimen may be a mammalian tissue. The tissue may be a tumor. The tissue may have been excised from the mammal before evaluation (ex-vivo) or may be evaluated in-situ (in-vivo).

It will be appreciated that numerous modifications to the abovementioned aspects and aspects of the present invention may be made without departing from the scope of the invention as defined in the appended claims. Moreover, any one or more of the above described preferred aspects could be combined with one or more of the other preferred aspects to suit a particular application.

Optional and/or preferred features may be used in other combinations beyond those described herein, and optional and/or preferred features described in relation to one aspect or aspect of the present invention may also be present in another aspect or aspect of the present invention, where appropriate.

The described and illustrated aspects and aspects are to be considered as illustrative and not restrictive in character, it being understood that only the preferred aspects and aspects have been shown and described and that all changes and modifications that come within the scope of the invention(s) as defined in the claims are desired to be protected. It should be understood that while the use of words such as "preferable", "preferably", "preferred" or "more preferred" in the description may suggest that a feature so described may be desirable, it may nevertheless not be necessary and aspects or aspects lacking such a feature may be contemplated as within the scope of the present invention as defined in the appended claims. In relation to the claims, it is intended that when words such as "a," "an," or "at least one," are used to preface a feature there is no intention to limit the claim to only one such feature unless specifically stated to the contrary in the claim.

BRIEF DESCRIPTION OF THE DRAWINGS

The above-mentioned and other features of this disclosure and the manner of obtaining them will become more apparent and the disclosure itself will be better understood by reference to the following description of aspects of the present disclosure taken in conjunction with the accompanying drawings, wherein:

FIG. 2A is a schematic diagram of a microscope system according to one aspect of the present disclosure;

DETAILED DESCRIPTION OF EMBODIMENTS

Figure 1B:
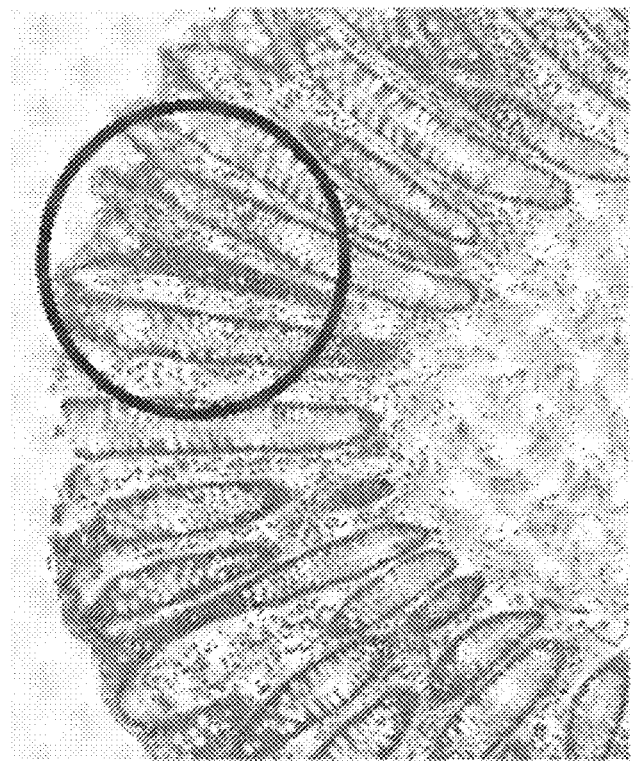
FIGS. 1A and 1B show views of a specimen using a microscope according to the present disclosure.

The aspects disclosed herein are not intended to be exhaustive or to limit the disclosure to the precise forms disclosed in the following detailed description. Rather, the aspects were chosen and described so that others skilled in the art may utilize their teachings.

As used herein, the modifier "about" or "approximately" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

As further described below, the present disclosure provides a microscope which works in a similar way to a simple fluorescent microscope with an attached imaging fiber optic. The microscope may also provide multiple channels for additional imaging of wavelengths or simultaneous ablation or treatment of tissues. The imaging fiber optic is composed of multiple smaller optic fibers that serve to transmit image data at a microscopic level. The microscope includes a light source(s) (exemplified as excitation energy 220 in FIGS. 2A and 2B) that emit light at a specific wavelength. The light is passed through a filter and condensing lens and is then channeled via a dichroic mirror into the objective. The light then passes through the fiber optic and onto the specimen. The specimen may be prepared by adding fluorescent dyes such as acridine orange to allow for better visualization. The tissue emits an excitation signal at a different wavelength that is transported via the imaging fiber optic to objective lens, dichroic mirror, emission filter and lens to be focused on the sensor of a camera. The fiber optic attachment to the objective lens offers 3 axis focus and positioning to allow focusing to the base of the fiber optic probe. The light source is housed in a structure that allows for the attachment of a heat sink, the condensing lens and the excitation filter.

As such, the present disclosure provides a method and apparatus for image acquisition of biological tissue using a fiber optic integrated with a simple fluorescent microscope. Unlike in-vivo or ex-vivo acquisition systems that utilize confocal fluorescent microscopy, the current system integrates a simple fluorescent set up for image acquisition. Also, the current system may integrate additional channels that may include ablative sources for simultaneous imaging and treatment of tissues. Compared to images resulting from confocal fluorescent microscopes, the images obtained via the present fluorescent microscopy are in their native three-dimensional architecture. As indicated above, the images are generated by exciting the tissue using continuous light emitted from a light source. The light is channeled to a magnifying objective lens and is then carried via an imaging optic fiber to the tissue. The light excites the tissue which in turns emits light at a different wavelength to be carried back through the imaging optic fiber, the objective to be channeled and focused on the image sensor of an image acquisition device such as a camera. The system may be used directly by applying the free end of the fiber optic in contact with the tissue and imaging the tissue without addition of fluorescent agents and using the inherent physical properties in the tissue and auto-fluorescence. A fluorescent dye may be applied to the tissue to enhance visualization. The dye may either be specific to a certain disease or attach to the cellular structures in a non-specific manner. The wavelength of the light emitted by the light source(s) is selected according to the excitation bandwidth of the dye used. Different dyes may be used with easily interchangeable filters and LEDs in the microscope. The objective magnification power may be changed with an accommodating focusable fiber optic adaptor.

The microscope may be composed of the following main components as is described in greater detail with reference to the figures of the present application.

Light Source Housing:

The light source housing holds a light emitting diode (LED) with an attached heat sink to dissipate heat. The wavelength of the light emitted is selected according to the characteristics of the dyes used on the tissue. The divergent light emitted from the LED is focused using a condenser lens, and filtered to a narrow bandwidth using an excitation filter. A slot allows for an easily interchangeable filter or lens if needed. The light then enters the filter cube.

Filter Housing:

In one aspect, the filter housing consists of a configuration that brings the excitation light produced from the light source at a right angle to the image acquisition axis. The excitation light may be reflected via a dichroic mirror placed at approximately a 45 degree angle. The dichroic mirror may be selected to be reflective to the wavelength of the excitation light produced by the LED and transparent/translucent to the light emitted by the tissue.

Objective and Fiber Optic:

The magnifying objective lens may be placed in line with the image acquisition axis. The light produced from the LED is reflected off the dichroic mirror and enters the base of the objective. The objective lens magnification power may vary. For example a 5×-40× objective lens may be used in certain aspects. A fiber optic may be then attached to the fiber optic holder (shown as 210 in FIGS. 2A and 2B) via a connector. The fiber optic used is an imaging fiber optic that includes a bundle composed of multiple smaller fibers. The number of fibers within the fiber optic may affect the resolution of the resultant image. The distance between the base of the fiber optic bundle may be adjustable via a screw mechanism to allow the focusing of the excitation light into the base of the fiber optic and the emitted light from the base of the same fiber optic from/to the objective lens. The base of the fiber optic bundle may also be translated perpendicular to the image acquisition axis to allow for fine adjustment of the fiber optic location within the objective's field of view. The free end of the fiber optic may be the placed in contact with the tissue to be imaged.

Camera Tube:

The camera tube contains an adaptor that permits the attachment of a complementary metal-oxide-semiconductor (CMOS)—such as a consumer DSLR camera—or a charge-coupled device (CCD) camera—such as scientific grade cameras—to the system. The tube may have a slot that accommodates the placement of a magnifying tube lens 216 and an emission filter 218 (shown in FIGS. 2A and 2B). The slots may permit easy interchangeability of a filter or lens, if needed, for example via a lens and filter tray. This may allow for the use of different fluorescent dyes with different excitation/emission wavelengths. The length of the tube is determined by the power of the magnifying lens to bring the image in focus in the camera.

As is also further described below, the microscope has several applications for in-vivo and ex-vivo tissue evaluation. Examples are provided below.

Ex-Vivo Specimens:

The first example is microscopic evaluation of disease at "grossing." Pathologists often rely on gross eye examination to determine dimensions, extension, and involvement of different anatomic structures, etc. of diseases such as tumors. This process is known as grossing. Accuracy of information obtained using gross examination is essential for staging and potentially correct treatment of patients. The microscope of the present disclosure permits the pathologist to directly and accurately obtain information about the tumor dimensions and extension at a microscopic level, that is otherwise not possible using prior art techniques. The present disclosure may even be used to obtain diagnoses and replace conventional methods of histology which often require several hours of tissue processing, embedding in paraffin wax, slicing and staining.

In a second example of ex-vivo tissue evaluation, the present disclosure provides improved sampling. The accuracy of evaluation of tissues by pathologists is often hindered by the gross sampling capabilities of the pathologist. Gross evaluation of a specimen to determine areas of the specimen to be sampled is an insensitive method of tissue sampling, however it is also the current method used in practice due to lack of the ability to directly evaluate tissues at the microscopic level. The present disclosure therefore offers a valuable tool to pathologists to evaluate tissue and uncover pathology that is otherwise missed with the naked eye.

In-Vivo Specimens:

In-vivo microscopy or microscopic evaluation of tumor margins in an intra-operative setting using the present disclosure allows the pathologist and surgeon the flexibility of microscopically evaluating specimens in their native three dimensional state "as is," and at an improved turnaround time. Evaluating the tissue in-vivo inside the patient is possible and allows for a dramatically enhanced localization of areas that may be involved with a tumor left behind after tumor removal (or positive margins). The present disclosure may be used to evaluate pathology in various clinical settings (such as cervical screening and oral examinations), and may also be incorporated in endoscopes to enhance endoscopic evaluation of tissues.

The addition of ablative energy sources in the additional channel within the microscope allows for the possibility of simultaneously imaging and treating the tissues. This allows for microscopic precision of the ablative energy in treating tissues such as tumors.

The present application provides applications of 3D design and printing as an inexpensive method for providing the framework of a fiber optic fluorescent microscope. 3D printing permits the development of highly customizable and unique structural and mechanical parts at extremely low costs. It also allows for the reproduction and modification of the microscope according to the present disclosure for various experiments and applications using off-the-shelf components.

Figure 1A:
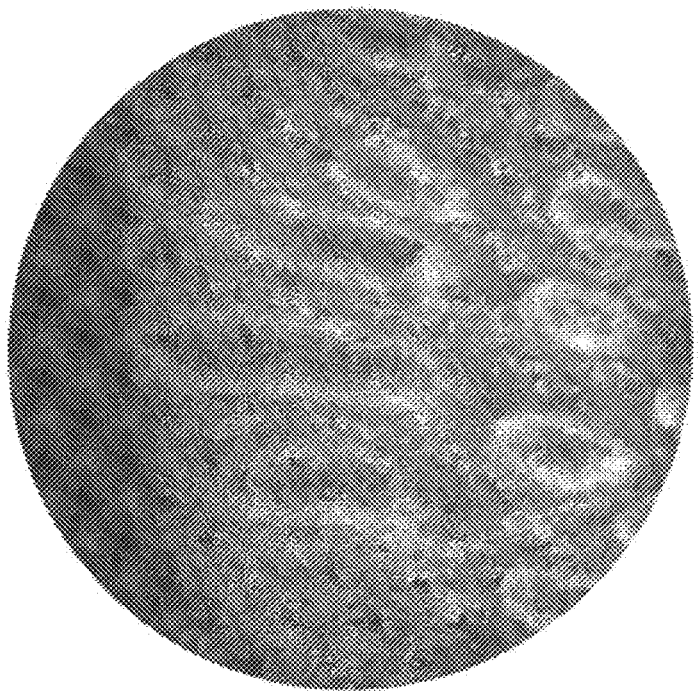

In one aspect of the present disclosure, an XYZ, da Vinci 1.0 3D printer is used for printing and Blender 3D modelling software was used for designing the parts. A Cannon T2i digital single lens reflection (DSLR) camera was used for the image acquisition, and a 20× objective, dichroic mirror, excitation and emission filters and tube lens are used as shown in the described figures. The filters and light emitting diode (LED) were selected for utility with acridine orange fluorescent dye, which was applied to the tissue to be viewed. An imaging fiber optic probe was attached to the objective using 3D printed parts for in-vivo or in-situ visualization. The other end was placed on the specimen, such as the specimen 5 exemplified in FIGS. 2A and 2B. Examples of the resulting images captured by the system are shown in FIGS. 1A and 1B. FIG. 1A, colonic crypts are shown using the present microscope after application of acridine orange, and FIG. 1B shows the corresponding hematoxylin and eosin processed slide.

The 3D printed components include a filter cube, which holds the dichroic mirror, objective and fiber optic holder that attaches to the filter cube, a camera tube and the light source housing. The 3D printed light source collimator was designed to accommodate the excitation energy 220 and heat sink and also holds an excitation filter and a condenser lens. A condenser lens was placed at a distance according to its focal length for partial collimation of the light from the LED light source to the base of the objective lens. The camera tube was designed with a base adaptor that inserts into the DSLR camera and has slots that hold the emission filter and tube lens. The camera tube and filter cube were printed in black plastic to minimize external light noise.

Figure 2B:
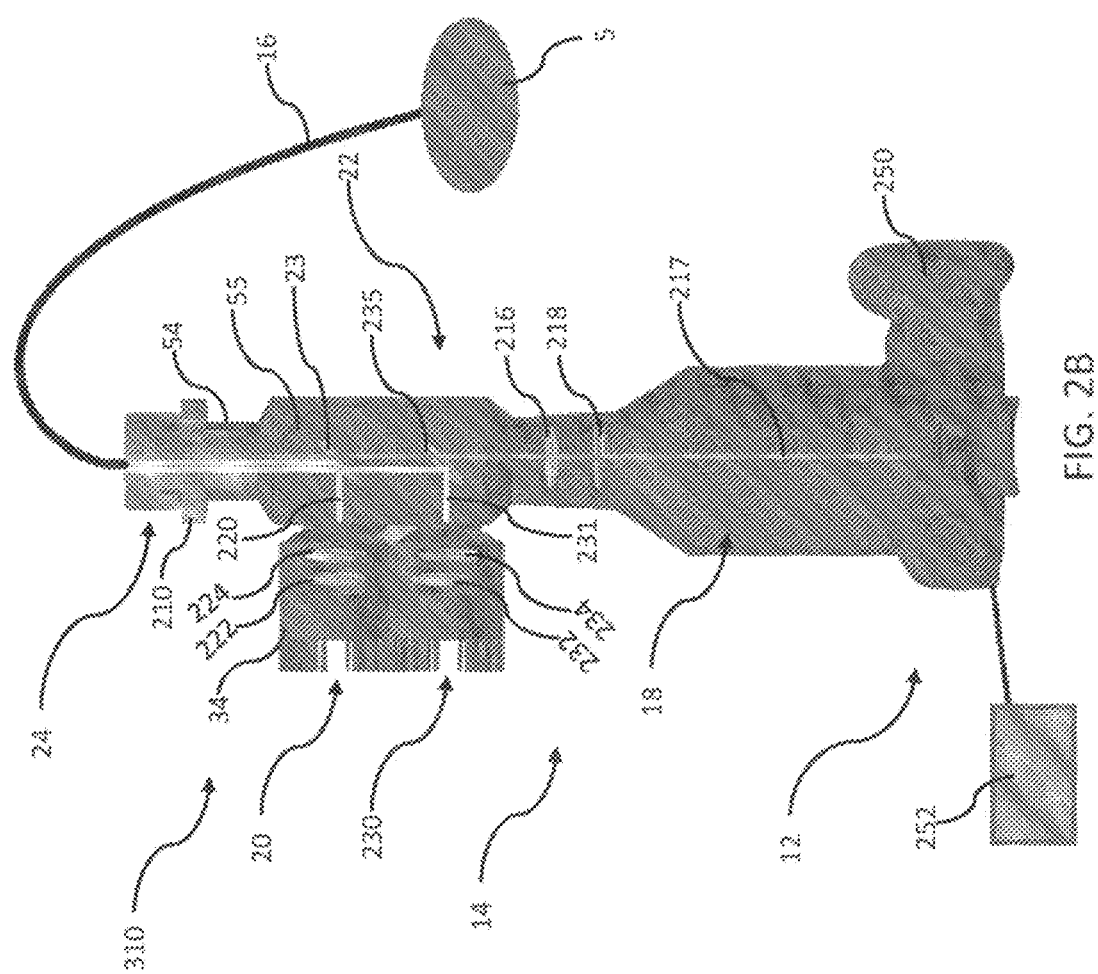
FIG. 2B is a schematic diagram of a microscope system comprising an ablative energy assembly according to one aspect of the present disclosure.

Referring now to FIGS. 2A and 2B, a microscope systems 10 and 310 respectively according to one aspect of the present disclosure are shown. Systems 10 and 310 may generally include an image acquisition device 12, such as the camera 250 described above, a microscope 14, and an imaging fiber optic 16. Microscope 14 generally includes a camera tube 18, a light source assembly 20, a filter cube 22, and an objective assembly 24. As shown, camera tube 18, light source assembly 20, and objective assembly 24 are each connected to filter cube 22. The emission light 217 from specimen 5 may travel from imaging fiber optic 16 and to the image acquisition device 12.

System 310, shown in FIG. 2B, may also include an ablative energy source assembly 230, which may comprise an ablative condenser 232 and an ablative filter 234. Ablative energy 231 may pass through the ablative condenser 232 and the ablative filer 234 and be reflected by ablative dichroic mirror 235. In various aspects of this disclosure, the inclusion of the ablative energy source assembly and the ablative dichroic mirror may allow for simultaneous diagnosis and treatment.

Figure 3:
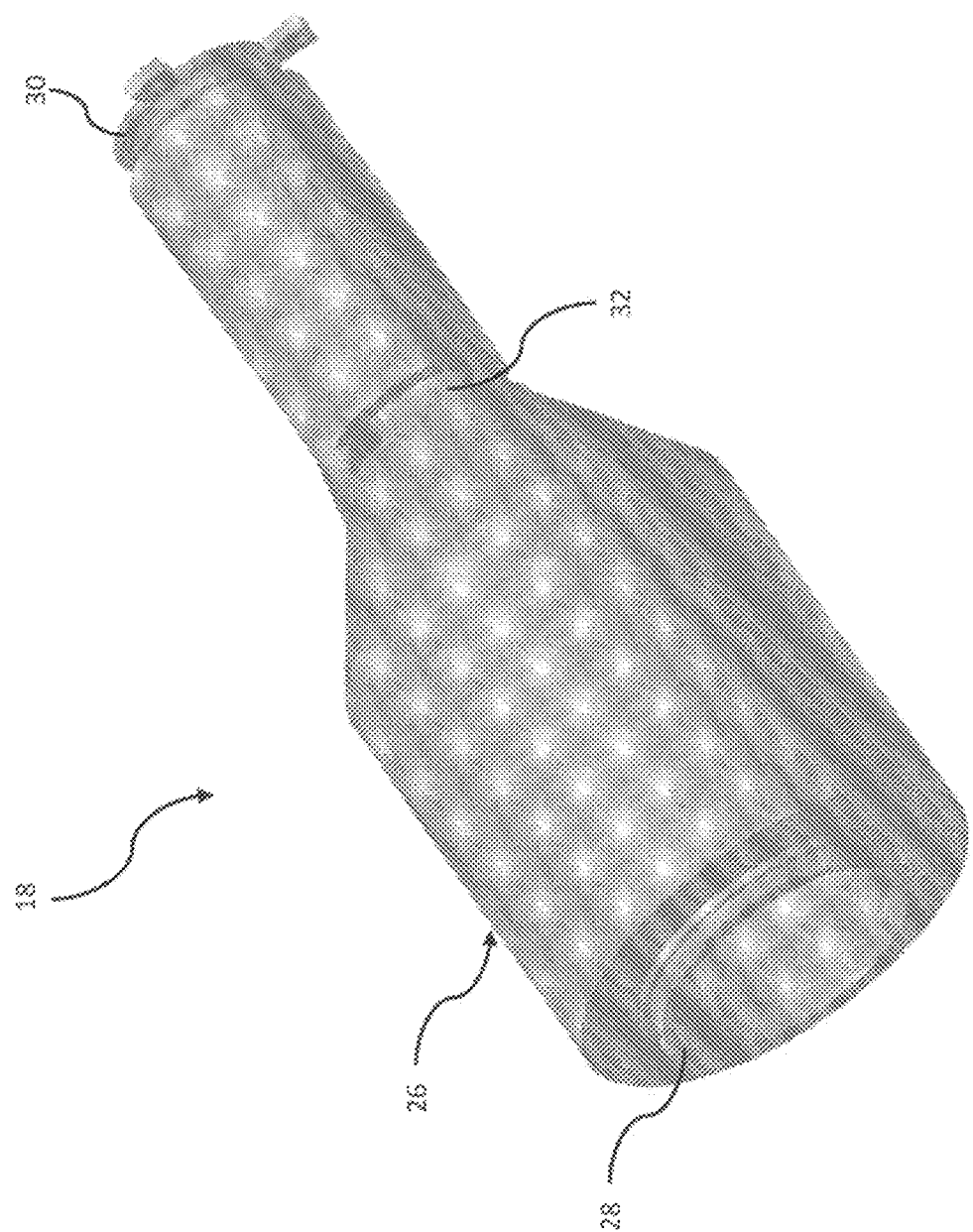
FIG. 3 is a perspective view of a camera tube of the microscope system of FIGS. 2A and 2B.

As best shown in FIG. 3, camera tube 18, which may be 3D printed as indicated above, includes a body 26 having one end 28 adapted to attach to image acquisition device 12 and another end 30 adapted to couple to filter cube 22. Body 26 further includes a slot 32 configured to receive a magnifying tube lens and an emission filter as depicted in FIGS. 2A and 2B. As indicated above, the overall length of camera tube 18 is determined by the power of the magnifying lens used to bring the image into focus.

Figure 4:
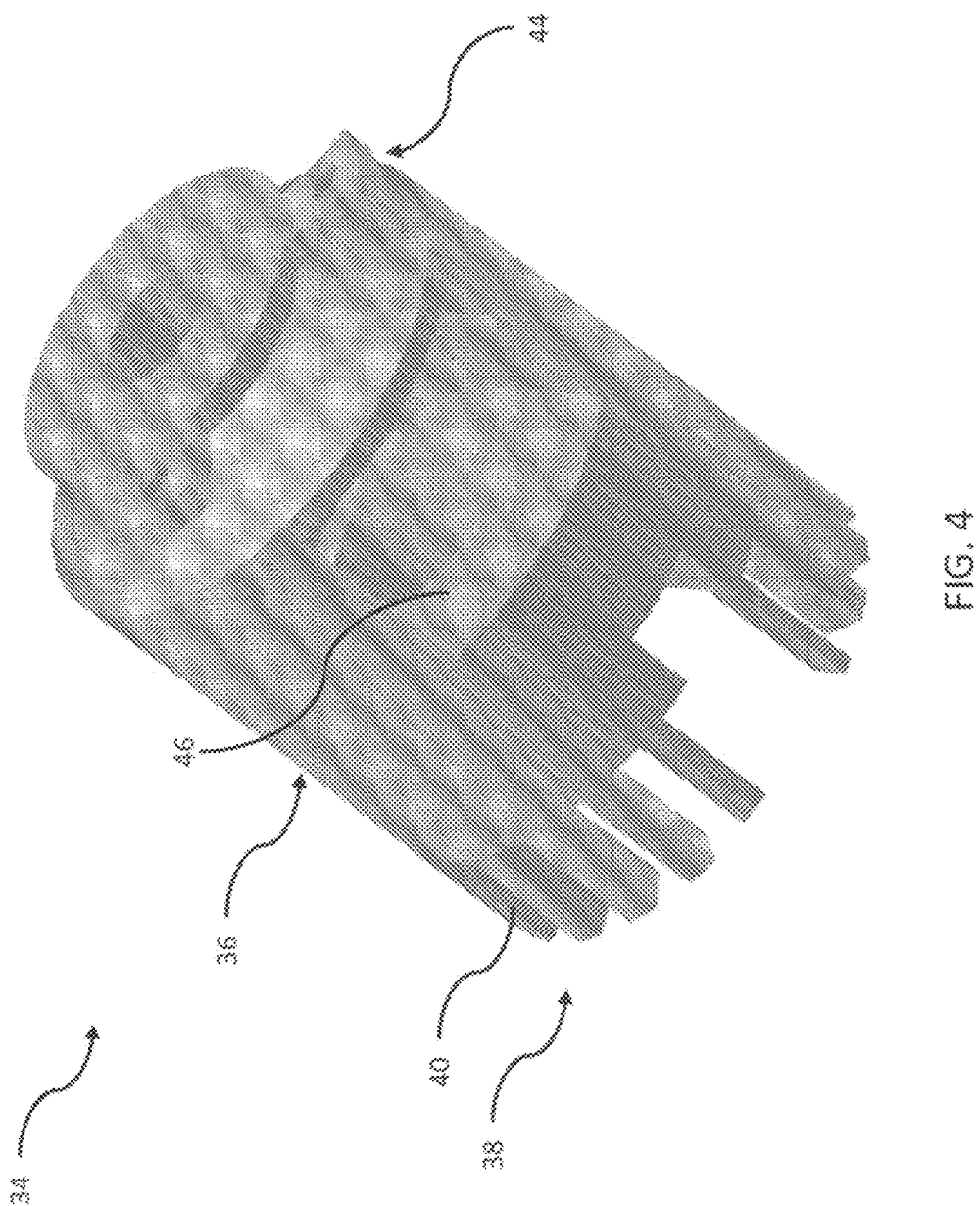
FIGS. 4 and 5 are perspective views of a light source housing of the microscope system of FIGS. 2A and 2B.
Figure 5:
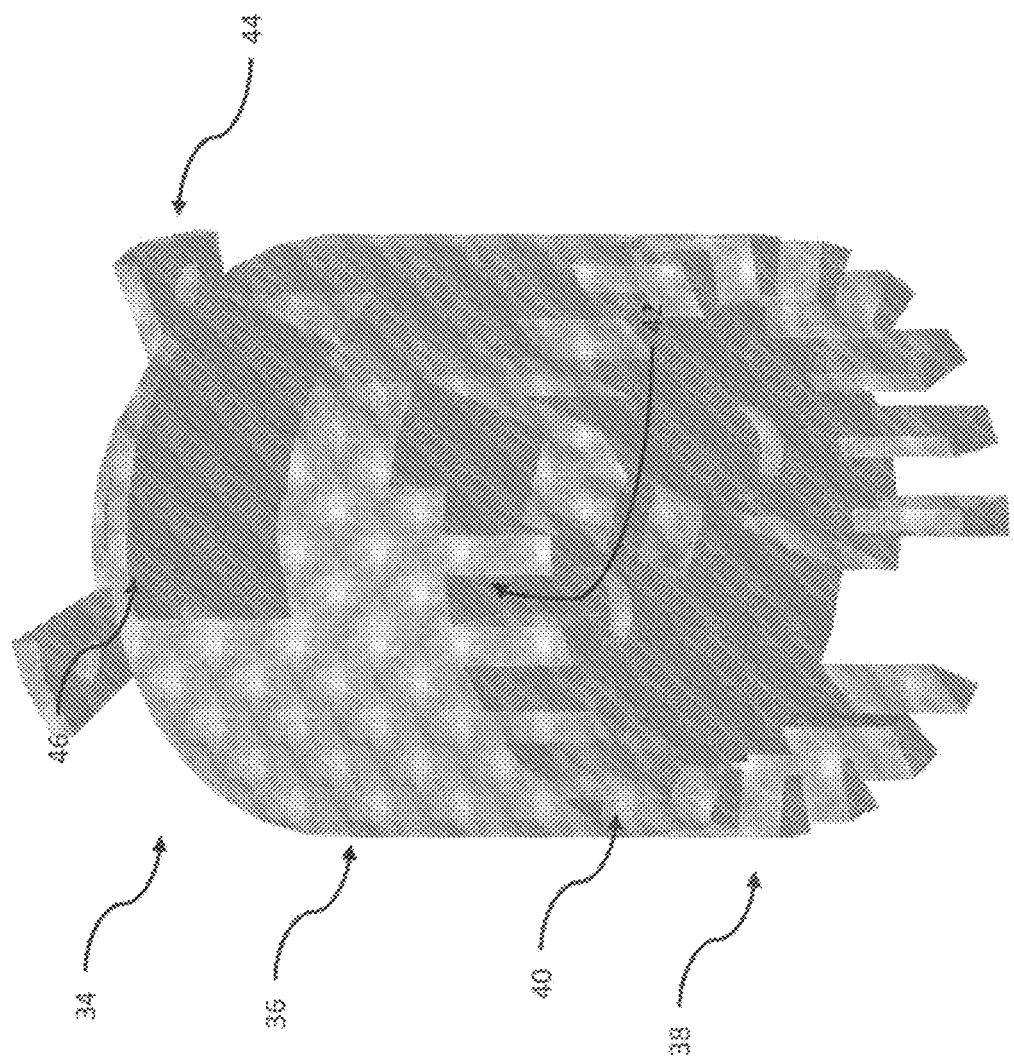

Referring now to FIGS. 4 and 5, a light source housing 34 of light source assembly 20 is shown. Light source housing 34, which may be 3D printed as indicated above, includes a body 36 having one end 38 with heat dissipation fins 40, an interior chamber 42 configured to receive a light source to produce excitation energy 220, which may pass through a condensing lens 222 and excitation filter 224, as depicted in FIGS. 2A and 2B, and another end 44 configured to couple with filter cube 22. As indicated above, the divergent light emitted from the LED may be focused using the condenser lens and filtered to the desired bandwidth using the excitation filter. Body 36 further includes a slot 46 to facilitate interchangeability of the lens and the filter.

Figure 6:
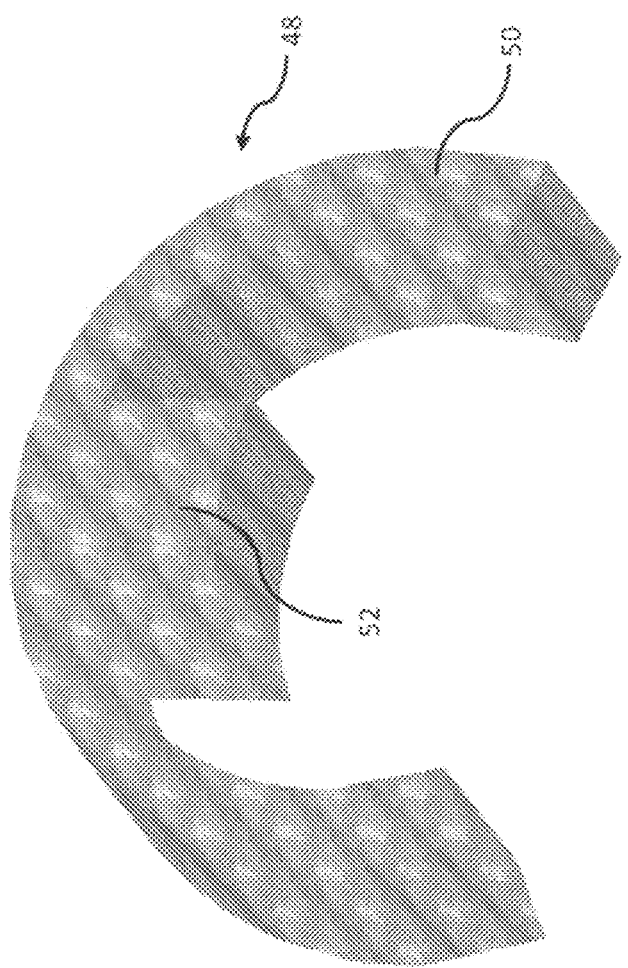
FIG. 6 is a perspective view of a light source slot cover of the microscope system of FIGS. 2A and 2B.

When system 10 is in operation, slot 46 may be covered by light source slot cover 48 depicted in FIG. 6. Light source slot cover 48, which may be 3D printed as indicated above, includes a curved body 50 which is sized to snap onto light source housing 34 and a projection 52 which is sized to fit into and cover slot 46 of the body 36 of light source housing 34.

Figure 7:
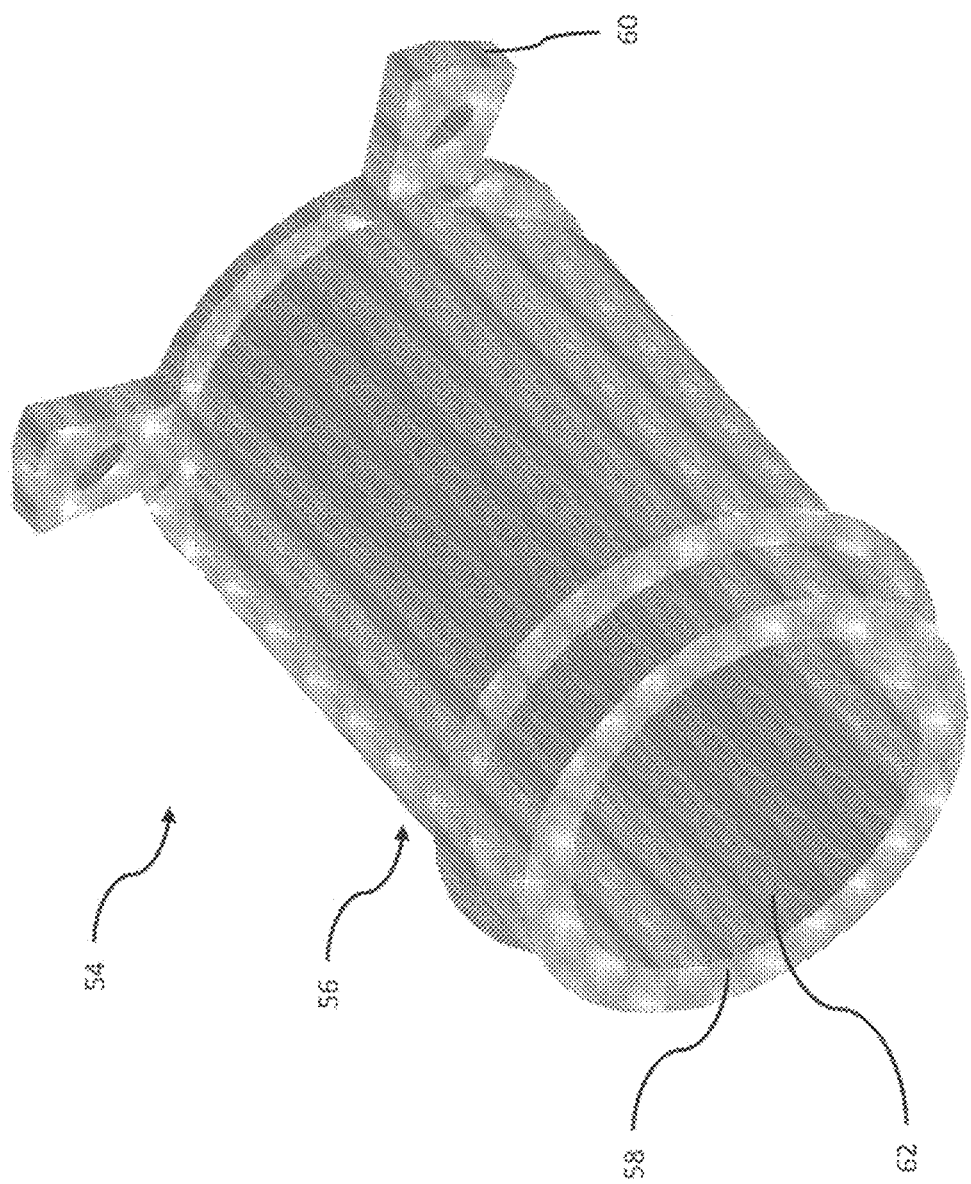
FIG. 7 is a perspective view of an objective holder of the microscope system of FIGS. 2A and 2B.

Referring now to FIG. 7, an objective holder 54 of objective assembly 24 is shown. Objective holder 54, which may be 3D printed as indicated above, includes a substantially cylindrical body 56 having one end 58 configured to couple to a fiber optic adapter as described below, another end 60 configured to couple with filter cube 22 and an interior chamber 62 for receiving the objective lens 55 as described above.

Figure 8:
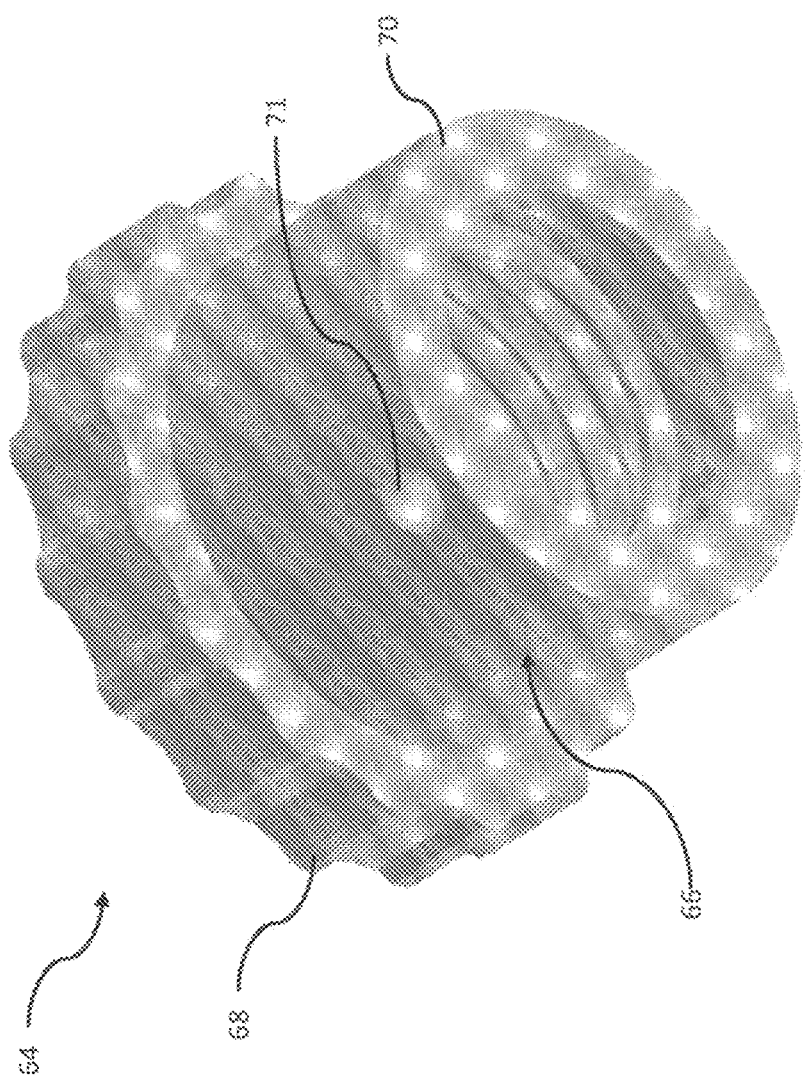
FIG. 8 is a perspective view of a fiber optic adapter of the microscope system of FIGS. 2A and 2B.

FIG. 8 depicts one aspect of a fiber optic adapter 64 of objective assembly 24. Fiber optic adaptor 64, which may be 3D printed as indicated above, includes a body 66 having one end 68 adapted to mate with end 58 of objective holder 54 and another end 70 adapted to receive imaging fiber optic 16. The fiber optic may be coupled with a female subminiature connector A ("SMA") threading that fits into a male counterpart housed within fiber optic adaptor 64. As indicated above, the base of imaging fiber optic 16 may be adjusted toward and away from the objective lens by rotating fiber optic adapter 64 to permit focusing of excitation light into imaging fiber optic 16 and the light emitted from the base of imaging fiber optic 16 to the objective lens. Furthermore, fiber optic adapter 64 may comprise adjustment groves 71, which may be configured to adjust the imaging fiber optic 16 in a plane perpendicular to the image acquisition axis.

Figure 9:
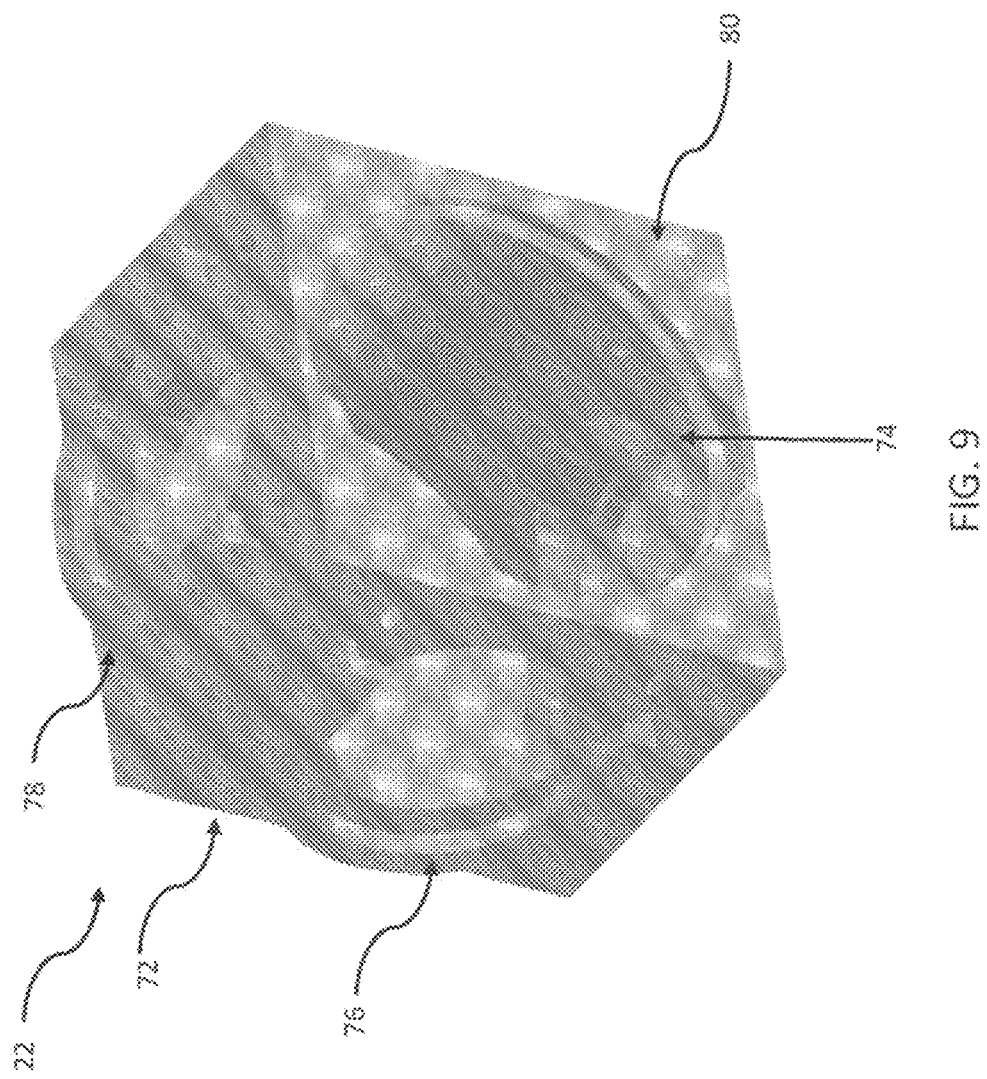
FIG. 9 is a perspective view of a filter cube of the microscope system of FIGS. 2A and 2B.

Referring now to FIG. 9, a filter cube 22 according to one aspect of the present invention is shown. Filter cube 22, which may be 3D printed as indicated above, includes a body 72 having a first side 74 configured to couple to end 30 of camera tube 18, a second side 76 configured to couple to end 44 of light source housing 34, a third side 78 configured to couple to end 60 of objective holder 54, and a fourth side 80 configured to receive a dichroic mirror holder as described below. In this configuration, excitation light from the LED enters filter cube 22 at a right angle to the image acquisition axis which extends longitudinally through objective holder 54. The dichroic mirror 23 (in FIGS. 2A and 2B) is held by the dichroic mirror holder (described below) at approximately a 45 degree angle relative to the entry angle of the excitation light to reflect the light through the objective holder 54 along the image acquisition axis. As indicated above, as the mirror is transparent to the light emitted by the tissue and acquired via image fiber optic 16, that light passes through the mirror and camera tube 18 to image acquisition device 12, which may display the captured image on display 252 of FIGS. 2A and 2B.

Figure 10:
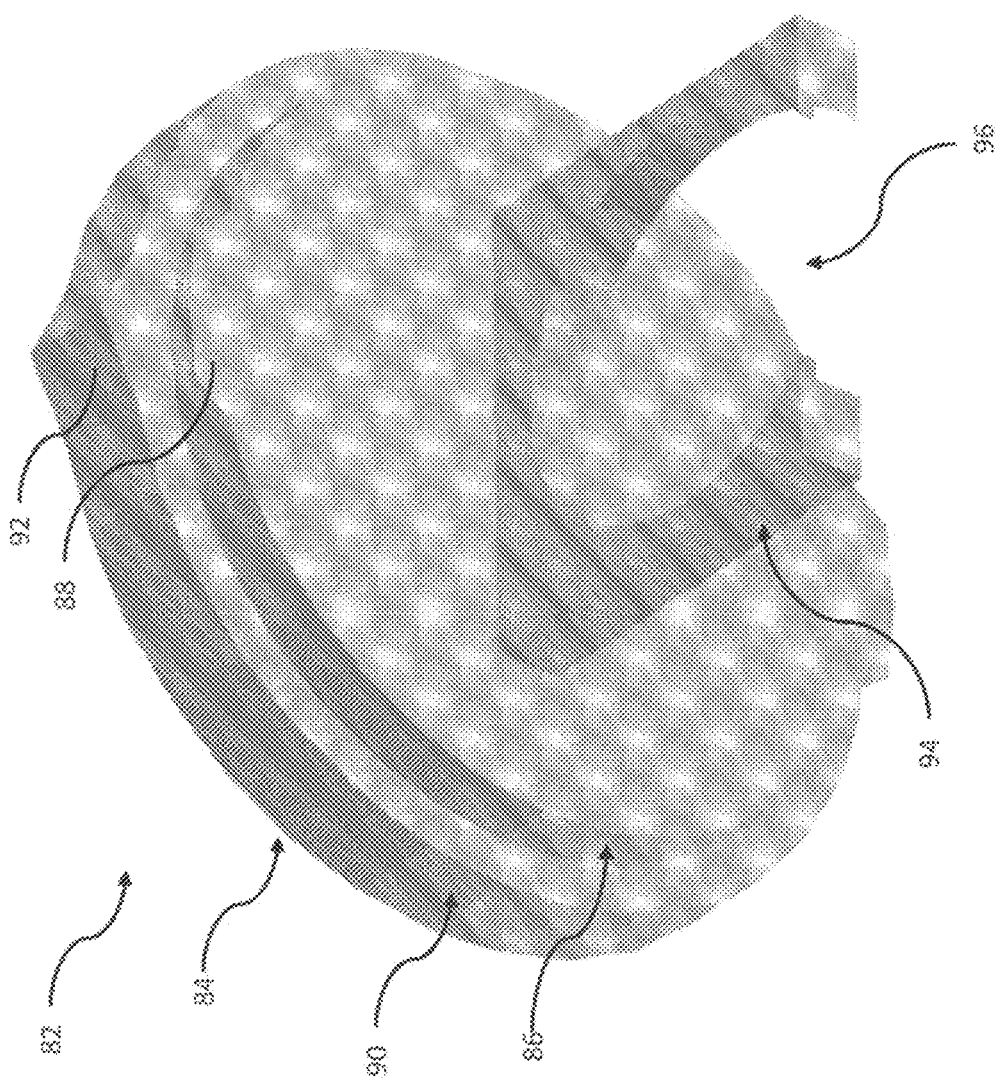
FIG. 10 is a perspective view of a dichroic mirror holder of the microscope system of FIGS. 2A and 2B.

FIG. 10 depicts one aspect of a dichroic mirror holder 82 of the present invention. Holder 82 includes a body 84 having an inner disc 86 with tabs 88, an outer disc 90 with tabs 92, and a mirror mount 94 that extends perpendicularly from inner disc 86. Mirror mount 94 includes an opening 96 for receiving the dichroic mirror. As should be apparent from the foregoing, inner disc 86 fits into the opening formed in fourth side 80 of filter cube 22 with tabs 88 in the annular slot formed around the opening and outer disc 90 and tabs 92 adjacent the outer surface of fourth side 90. In this manner, mirror mount 94 is supported within filter cube 22 and the angle of mirror mount 94 (and therefore the dichroic mirror) may be adjusted by rotating holder 82 within the opening of fourth side 80.

In the foregoing specification, specific aspects of the present disclosure have been described. However, one of ordinary skill in the art will appreciate that various modifications and changes can be made without departing from the scope of the disclosure as set forth in the claims below. Accordingly, the specification and figures are to be regarded in an illustrative rather than a restrictive sense, and all such modifications are intended to be included within the scope of disclosure. The benefits, advantages, solutions to problems, and any element(s) that may cause any benefit, advantage, or solution to occur or become more pronounced are not to be construed as critical, required, or essential features or elements of any or all the claims. The disclosure is defined solely by the appended claims including any amendments made during the pendency of this application and all equivalents of those claims as issued. Although the invention has been described in detail with reference to certain preferred aspects, variations and modifications exist within the spirit and scope of the invention as described and defined in the following claims.

What is claimed is:

1. A microscope comprising:
    a filter cube having a first side coupled to a light source housing comprising a light emitting diode and a second side coupled to an objective holder, the objective holder coupled to a fiber optic holder configured to receive a fiber optic;
    a tube coupled to a third side of the filter cube, the tube configured to mechanically communicate with an image acquisition device; and
    an ablative energy source assembly coupled to the filter cube, wherein the filter cube comprises a channel for ablative energy;
    wherein the filter cube, the tube, and the objective holder define an image acquisition axis.

2. The microscope of claim 1, wherein the filter cube comprises a dichroic mirror.

3. The microscope of claim 2, wherein the dichroic mirror forms an angle of about 45 degrees with the image acquisition axis.

4. The microscope of claim 1, wherein the objective is placed in line with the image acquisition axis.

5. The microscope of claim 1, wherein the fiber optic holder is configured to move along the image acquisition axis.

6. The microscope of claim 5, wherein the fiber optic holder is configured to move along the image acquisition axis via a screw mechanism.

7. The microscope of claim 1, wherein the fiber optic comprises a bundle of multiple smaller optic fibers.

8. The microscope of claim 1, further comprising a filter between the light emitting diode and the image acquisition axis.

9. The microscope of claim 1, further comprising a condensing lens between the light emitting diode and the image acquisition axis.

10. The microscope of claim 1, further comprising a heat sink in mechanical communication with the light source housing.

11. The microscope of claim 1, wherein the tube is configured to accommodate a placement of at least one of a magnifying tube lens, an emission filter, or both.

12. The microscope of claim 11, wherein the tube is configured to interchange magnifying tube lenses, emission filters, or both.

13. A microscope comprising:
    a body including:
        a light source housing comprising a light emitting diode that emits a light at a specific wavelength;
        a tube configured to mechanically communicate with an image acquisition device; and
        an objective holder coupled to a fiber optic holder configured to receive an imaging fiber optic, the imaging fiber optic comprising a bundle of optic fibers, where a diameter of each optic fiber in the bundle is smaller than a diameter of the imaging fiber optic and where the imaging fiber optic has a distal tip configured to be moveably disposed adjacent a fluorescently dyed biological specimen;
    wherein the tube and the objective holder define an image acquisition axis, and where the imaging fiber optic carries a light from the light emitting diode of the body to the fluorescently dyed specimen that causes the fluorescent dye to fluoresce, where a light is reflected from the fluorescently dyed specimen having a different, specific wavelength from the light emitted by the light emitting diode, and where the imaging fiber optic carries the light that is reflected from the fluorescently dyed specimen to the image acquisition device to generate an image of the specimen in a native, three-dimensional state.

14. A microscope according to claim 13, wherein the imaging fiber optic carries light from a sample to the image acquisition device.

15. A microscope according to claim 13, wherein the imaging fiber optic carries light from the light source to the image acquisition device.

16. A microscope according to claim 13, further comprising a filter cube and a channel for ablative energy.

17. The microscope of claim 1, the light source housing including a light source housing slot configured to selectively receive a filter or a lens.

18. The microscope of claim 17, the light source housing slot configured to receive a projection of a light source housing slot cover.

19. The microscope of claim 1, the tube having a tube slot configured to selectively receive a filter or a lens.

20. The microscope of claim 19, the tube slot comprising a tray for selectively receiving the filter or the lens.

\* \* \* \* \*